(12) United States Patent
Sobue

(10) Patent No.: US 8,613,739 B2
(45) Date of Patent: Dec. 24, 2013

(54) MEDICAL TUBING CONNECTION ASSEMBLY

(75) Inventor: Katsuyoshi Sobue, Tokyo (JP)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 0 days.

(21) Appl. No.: 13/328,935

(22) Filed: Dec. 16, 2011

(65) Prior Publication Data
US 2013/0158521 A1    Jun. 20, 2013

(51) Int. Cl.
| | |
|---|---|
| A61M 25/16 | (2006.01) |
| A61M 25/18 | (2006.01) |
| A61M 39/00 | (2006.01) |
| A61M 39/10 | (2006.01) |
| F16B 7/10 | (2006.01) |
| F16B 7/00 | (2006.01) |
| F16B 5/00 | (2006.01) |
| B25G 3/00 | (2006.01) |
| B25G 3/28 | (2006.01) |
| B25G 3/30 | (2006.01) |

(52) U.S. Cl.
USPC ........ 604/533; 604/534; 604/905; 403/109.4; 403/118; 403/299; 403/309; 403/359.3

(58) Field of Classification Search
USPC .......... 604/533–539, 905, 910, 921; 403/5–6, 403/24, 109.4, 110, 118, 182–184, 299, 403/307–311, 359.3, 257–261
See application file for complete search history.

(56) References Cited

U.S. PATENT DOCUMENTS

| | | | | |
|---|---|---|---|---|
| 6,585,533 | B1* | 7/2003 | Sullivan et al. | 439/254 |
| 7,240,926 | B2* | 7/2007 | Dalle et al. | 285/308 |
| 7,347,458 | B2* | 3/2008 | Rome et al. | 285/384 |
| 2007/0076401 | A1 | 4/2007 | Carrez et al. | |
| 2010/0036365 | A1 | 2/2010 | Becker | |

FOREIGN PATENT DOCUMENTS

| | | |
|---|---|---|
| FR | 2863162 | 6/2005 |
| GB | 2379253 | 3/2003 |

OTHER PUBLICATIONS

International Search Report and Written Opinion for corresponding International Application No. PCT/US2012/069377, mailing date Jul. 30, 2013.

* cited by examiner

*Primary Examiner* — Nicholas Lucchesi
*Assistant Examiner* — Rebecca E Eisenberg
(74) *Attorney, Agent, or Firm* — Marshall, Gerstein & Borun LLP

(57) ABSTRACT

A medical tubing connector pair includes a female tubing connector, and a male tubing connector. The female tubing connector has an external thread and the male tubing connector has an internal thread, the external and internal threads threadingly engaged to secure the female and male tubing connectors together. The internal thread is made from a flexible material to permit the female and male tubing connectors to be connected to or disconnected from each other without rotation of the tubing connectors relative to each other.

7 Claims, 3 Drawing Sheets

MEDICAL TUBING CONNECTION ASSEMBLY

BACKGROUND

This patent relates to a medical tubing connection assembly. In particular, this patent relates to a medical tubing connection assembly including a pair of connectors that may be connected or disconnected with or without relative rotational motion between the connectors.

Medical tubing connectors play a significant role in the delivery of medical fluids to a patient. A medical tubing connection assembly typically includes a pair of components including female connector and a male connector with a tube-like inlet piece. The connectors may also include additional components such as interior valves and the like.

In applications where the tubing connectors are to be connected for a prolonged period of time or where an accidental disconnect is undesirable, a locking or securing mechanism is generally incorporated into the connector pair. Conventionally, a collar is disposed about the tube-like inlet piece (which may be a luer tip, according to certain embodiments) of the male connector, the collar having an internal thread formed on an inner surface of the collar. Additionally, an external thread is formed on a housing of the female connector. The male and female connectors are secured together by rotating the connectors relative to each other to threadingly engage the mating threads of the male and female connectors.

Under certain circumstances, it may be advantageous to provide a mechanism or machine to bring the connector pair together with a minimum of user intervention (a so-called "assist device" or "changer"). For example, the machine may have a holder to receive the female connector, and a holder to receive the male connector. The machine also includes a mechanism to bring the connectors together and then rotate the connectors relative to each other to secure the connectors together. Given the series of motions involved in such an operation, including translational motion (to bring the connectors together) and rotational motion (to bring the threads together), the operating mechanism of such a machine can be considerably complex. As a consequence, these machines tend to be expensive and relatively bulky (in terms of size and weight) because of the complicated mechanism required to perform these actions.

Preferably, the connectors would be brought together and secured through the use of a single motion, for example an axial motion. This would permit a simpler mechanism to be used, with an accompanying reduction in the expense, size, and weight of the machine. Thus, a modified tubing connector has been designed that lacks the threaded engagement present in other medical tubing connection assemblies. Because the threads are not present, the connectors do not need to be rotated when securing the connectors together. This permits a simplified action for bringing the connectors together, and consequently a machine of simplified design.

Of course, this also means that the modified connectors, well-suited for the simplified machine, may not be readily used in applications and settings (e.g., manual use) where the conventional tubing connectors with threaded engagement are typically used. Consequently, a healthcare provider may need to keep both types of medical tubing connection assemblies on hand, which increases the overall size of inventory required and the potential for incompatibilities between the connector and the associated equipment at the time of use through inventory confusion.

As set forth in more detail below, the present disclosure sets forth an improved assembly embodying advantageous alternatives to the conventional devices and approaches discussed above.

SUMMARY

According to an aspect of the present disclosure, a medical tubing connector pair includes a female tubing connector and a male tubing connector. The female tubing connector has an external thread and the male tubing connector has an internal thread, the external and internal threads threadingly engaged to secure the female and male tubing connectors together. The internal thread is made from a flexible material to permit the female and male tubing connectors to be connected to or disconnected from each other without rotation of the tubing connectors relative to each other.

According to another aspect of the present disclosure, a medical tubing connector pair includes a female tubing connector and a male tubing connector. The female tubing connector has an external thread and the male tubing connector has an internal thread, the external and internal threads threadingly engaged to secure the female and male tubing connectors together. The male tubing connector includes a collar made of a flexible material, the internal thread defined on an inner surface of the collar. The connector pair has a first mode of engagement wherein the external and internal threads are rotated relative to each other into or out of engagement, and a second mode of engagement wherein the collar is deflected by a squeezing or expanding force to permit the external and internal threads to move axially relative to each other into or out of engagement.

Additional aspects of the disclosure are defined by the claims of this patent.

BRIEF DESCRIPTION OF THE FIGURES

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 5:
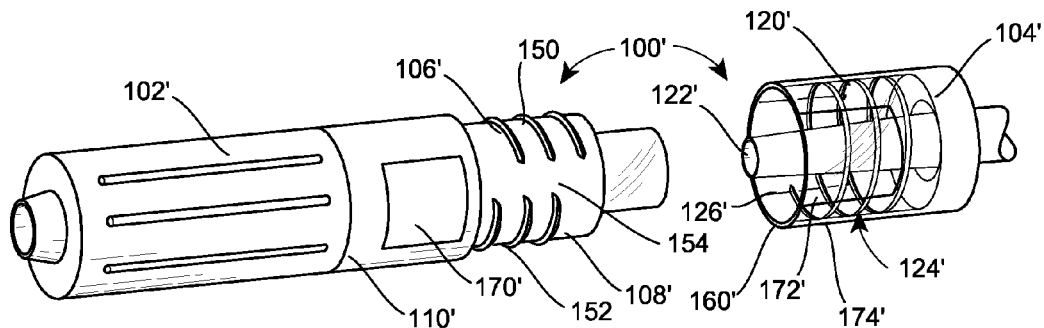
FIG. 5 is a perspective view of a medical tubing connector pair according a second embodiment of the present disclosure with the connectors disconnected from each other.
Figure 6:
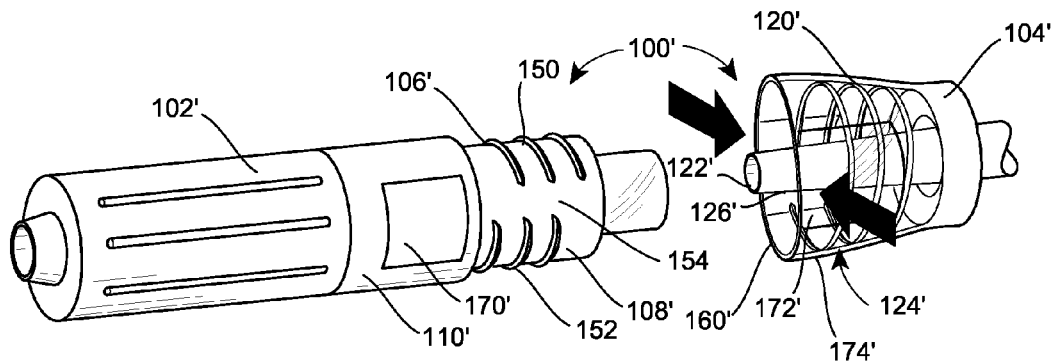
FIG. 6 is a perspective view of a medical tubing connector pair of FIG. 4 with the collar squeezed to facilitate translational connection.
Figure 7:
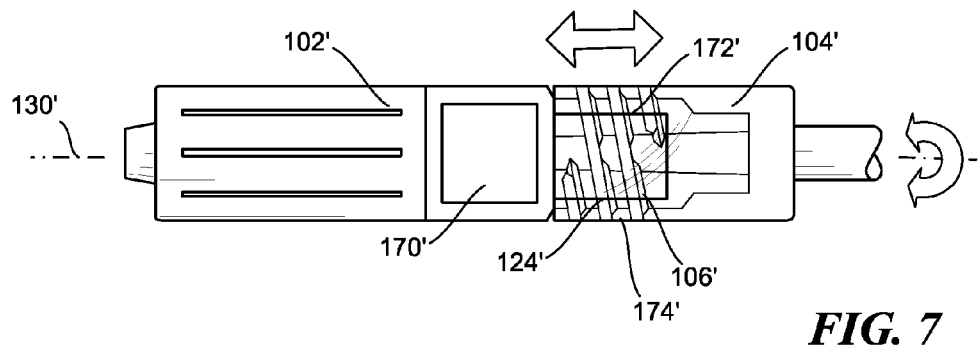
FIG. 7 is a side view of the medical tubing connector pair of FIG. 4 illustrating connection according to a first mode and a second mode of operation.

FIGS. 1-4 illustrate a first embodiment of a medical tubing connector pair 100 according to the present disclosure, while FIGS. 5-7 illustrate second embodiment of a medical tubing connector pair 100' according to the present disclosure. Because the second embodiment of the tubing connector pair 100' shares numerous features in common with the tubing connector pair 100, similar features will be referred to using similar reference numerals, with those features of the embodiment of FIGS. 5-7 distinguished from those features of the embodiment of FIG. 1-4 through the use of a prime.

Figure 1:
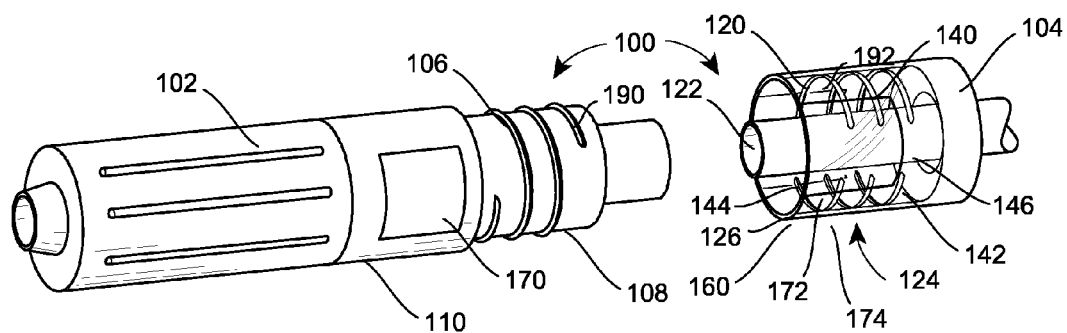
FIG. 1 is a perspective view of a medical tubing connector pair according a first embodiment of the present disclosure with the connectors disconnected from each other.
Figure 2:
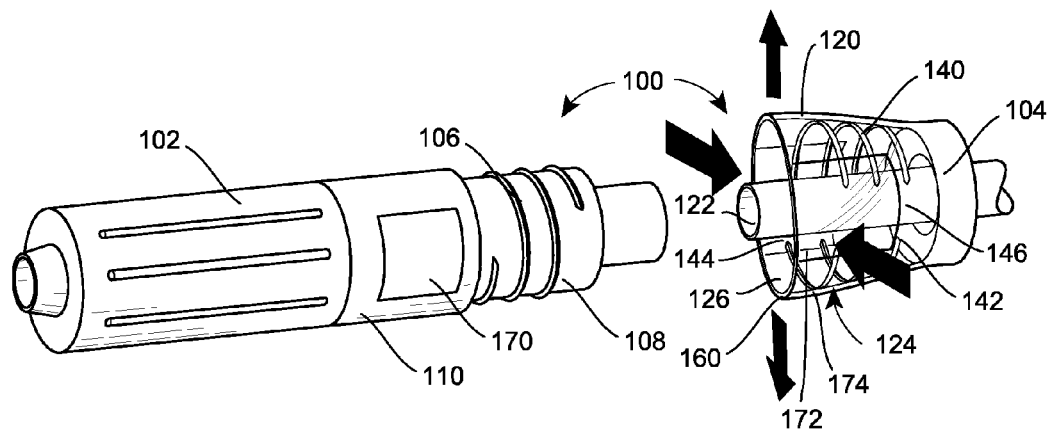
FIG. 2 is a perspective view of a medical tubing connector pair of FIG. 1 with the collar squeezed to facilitate translational connection.
Figure 3:
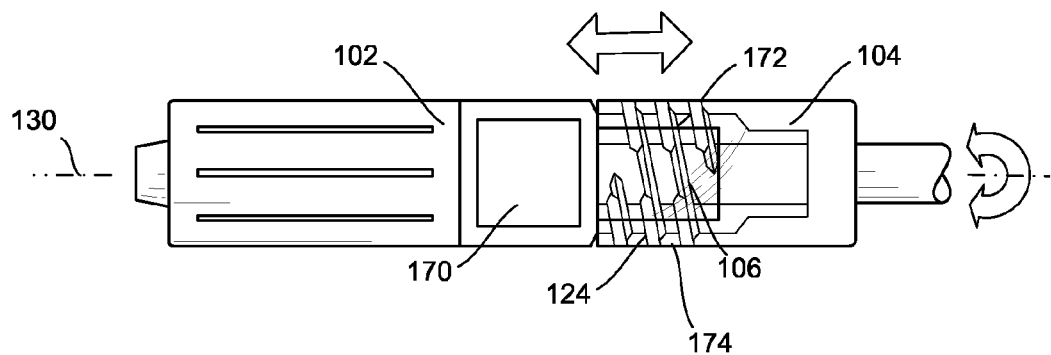
FIG. 3 is a side view of the medical tubing connector pair of FIG. 1 illustrating connection according to a first mode and a second mode of operation.
Figure 4:
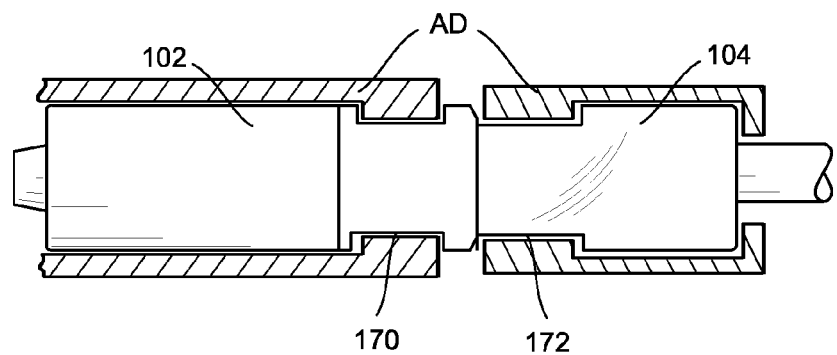
FIG. 4 is a partial cross-sectional view of the medical tubing connector pair of FIG. 1 in combination with an assist device, illustrating the cooperation between features of the medical tubing connector pair and the assist device.

Referring first to the first embodiment illustrated in FIGS. 1-3, the medical tubing connector pair 100 includes a first tubing connector 102 and a second tubing connector 104. The first tubing connector 102 may be a female tubing connector, as illustrated. The second tubing connector 104 may be a male tubing connector.

Each of the first and second tubing connectors 102, 104 may have a mating thread formed on a surface of the tubing connector 102, 104. In particular, the first tubing connector 102 has an external thread 106 formed on an outer surface 108 of a housing 110. In a similar fashion, the second tubing connector 104 includes a collar 120 disposed about a male luer tip 122, the collar 120 having an internal thread 124 formed or defined on an inner surface 126. The external thread 106 and the internal thread 124 threadingly engage to secure the first and second tubing connectors 102, 104 together, as illustrated in FIG. 3.

According to the present disclosure, the collar 120 is made from a flexible material, such as an elastic material. With the collar 120 made from a flexible material, the first and second connectors 102, 104 may be connected to or disconnected from each other without rotation of the first and second tubing connectors 102, 104 relative to each other. That is, according to a first mode of operation, such as is illustrated by a double-headed curved arrow in FIG. 3, the first and second tubing connectors 102, 104 are rotated relative to each other, thereby threadingly engaging the threads 106, 124 and securing the first and second tubing connectors 102, 104 to each other. However, according to a second mode of operation, such as is illustrated by a double-headed straight arrow in FIG. 3, the first and second tubing connectors 102, 104 may be moved axially or translated along a common axis 130 with the collar 120 made of the flexible material deflecting so as to permit the collar 120 to move over the threads on the connector 102 without the threads 106 engaging the threads 124.

The movement of the collar 120 over the threads on the connector 102 may be facilitated by having at least one of the external and internal threads 106, 124 be discontinuous. That is, a discontinuous thread would be one that does not complete one or more revolutions about the surface on which it is defined. For instance, threaded regions of the at least one of the external and internal threads 106, 124 may be defined on opposing side regions of the connector 102, 104 with non-threaded regions disposed between the threaded regions of the at least one of the external and internal threads 106, 124 defined on opposing sides of the connector 102, 104. It will be recognized that this is simply an exemplary embodiment of a potentially discontinuous thread, and should not be taken as limiting a discontinuous thread to only such an embodiment.

For instance, in the embodiment of the tubing connector pair 100 illustrated in FIG. 1, the internal thread 124 defined on the inner surface 126 of the connector 104 is discontinuous. In particular, the internal thread 124 has two threaded regions 140, 142 that are defined on opposing sides of the connector 104 with non-threaded regions 144, 146 disposed between the threaded regions 140, 142 of the internal thread 124 and defined on opposing sides of the connector 104. In a similar fashion, in the embodiment of the tubing connector pair 100' illustrated in FIG. 5, the external thread 106' defined on the outer surface 108' has two threaded regions 150, 152 that are defined on opposing sides of the connector 102' with non-threaded regions (e.g., at 154) disposed between the threaded regions 150, 152 of the external thread 106' and defined on opposing sides of the connector 102.

According to certain embodiments, such as those illustrated in FIGS. 1-7, in addition to at least one of the external and internal threads 106, 124 being defined with discontinuous regions, the other of the external and internal threads 106, 124 is continuous. That is, a continuous thread is one that completes one or more revolutions about the surface on which it is defined. It will be recognized that it is not necessary for the other of the external threads 106, 124 to be continuous according to all embodiments of the present disclosure. For example, the thread 106 may be discontinuous, but the non-threaded regions between the threaded regions of this discontinuous thread may be smaller than the non-threaded regions of the discontinuous thread 124. Therefore, while connector pairs 100, 100' have been illustrated wherein at least one of the external and internal threads 106, 124 includes discontinuous threaded regions and the other of the external and internal threads 106, 124 is continuous, this is simply an exemplary embodiment of the present disclosure.

As mentioned previously, the collar 120 is formed of a flexible material. According to such an embodiment, the collar 120 may be grasped to cause the wall 160 which defines the collar 120 to deform as illustrated in FIG. 2, and thereby assist in the radially outward deflection of the thread 124 to permit the connectors 102, 104 to connect to and disconnect from each other. Similar remarks may be made regarding the internal thread 124' of the second embodiment.

In fact, the first and second tubing connectors 102, 104 may each have thumb or finger pads 170, 172 formed thereon. In particular, the pads 170 may be formed on the outer surface 108 of the housing 110 of the first tubing connector 102, while the pads 172 may be formed on an outer surface 174 of the wall 160 of the collar 120 of the second tubing connector 104. These finger pads 170, 172 may assist in gripping the first and second tubing connectors 102, 104 in either mode of operation. The finger pads 172 on the second tubing connector 104 may also assist in application of a squeezing force to the wall 160 of the collar 120 to cause the deflection of the collar 120.

Additionally, the finger pads 170, 172 may be disposed on the first and second tubing connectors 102, 104 to facilitate alignment of the connectors 102, 104 when loaded into an assist device. It is believed that better alignment and positioning of the first and second tubing connectors 102, 104 will increase the likelihood that the threads 106, 124 of the connectors 102, 104 will substantially or fully engage (engage to a proper or desired depth, e.g.) when the connectors 102, 104 are brought together axially by the assist device. To this end, the pads 170, 172 may be defined by a depression or cut-out formed in the housing 110 or the wall 160 of the collar 120, thereby defining a pair of opposing planar surfaces about the otherwise generally cylindrical housing 110 or collar 120 that cooperate with features of the assist device AD to improve alignment and limit movement of the connectors 102, 104 relative to the assist device AD. See, e.g., FIG. 4. However, the finger pads 170, 172 may take other shapes or forms as well.

Upon connection between the connectors 102, 104, the luer tip 122 of the male connector 104 will sealingly engage the internal surface of the female connector 102 to provide a path for fluid communication between the connectors 102, 104.

Having thus described the structure of the tubing connector pair 100, the modes of operation of the tubing connector pair 100 are now the discussed with reference to FIG. 3.

FIG. 3 illustrates a first mode of operation (or engagement) for the above-mentioned tubing connector pair 100. According to this first mode of operation, the connectors 102, 104 are brought together such that the threads 106, 124 abut at their ends 190, 192. With rotation of the connectors 102, 104 relative to each other (as represented by the double-headed curved arrow), the threads 106, 124 matingly engage each other, and thereby secure the connectors 102, 104 to each other. It will be recognized that the relative rotation of the connectors 102, 104 may be achieved by rotating either one or both of the connectors 102, 104 (or more particularly, the threads 106, 124) relative to the other. It will also be recognized that the flexible nature of the thread 106, 124 is not necessary to the first mode of operation in that the threads 106, 124 matingly engage according to the nature and shape of the threads 106, 124. As a variant of this mode of operation, the collar 120 may be permitted to rotate around the male luer tip 122 so that the male luer tip 122 does not have to be rotated.

Alternatively, FIG. 3 also illustrates a second mode of operation (or engagement) for the above-mentioned tubing connector pair 100. According to the second mode of operation, the connectors 102, 104 are brought together such that the threads 106, 124 abut at their ends 190, 192. However, the connectors 102, 104 are not rotated relative to each other. Instead, a squeezing force may be applied to the collar 120 at the section of the collar 120 having the discontinuous thread as illustrated in FIG. 2. Alternatively, an expanding force may be generated when threads 124 of the collar 120 run over the threads 106 of the female tubing connector 102. As a consequence, the threaded region 124 (according to the illustrated embodiment) is deflected axially outward for a distance that allows the connectors 102, 104 move axially relative to each other. Once the squeezing or expanding force has been removed from the collar 120, the collar 120 will recover and the threads 106, 124 matingly engage each other to resist axial separation of the connectors 102, 104. Similarly, a squeezing or expanding force may be applied to the collar 120 to disconnect the connectors 102, 104. In this fashion, the second mode of operation is a so-called "push and pull" operation, contrasted with the "screw" operation of the first mode of operation.

As mentioned above, one major difference between the tubing connector pair 100 and the tubing connector pair 100' relates to which of the illustrated threads 106', 124' is illustrated as discontinuous. According to the embodiment of the tubing connector pair 100', the external thread 106' of the connector 102' is discontinuous, with regions 150, 152 separated by spaces (one of which is illustrated at 154). This may be compared with the configuration of the threads 124 of the pair 100, which has the regions 140, 142 separated by the non-threaded regions 144, 146. Despite this structural difference, it will be recognized that the modes of operation illustrated in FIG. 7 are similar to those of the modes illustrated in FIG. 3.

It will be recognized that the connector pair (and individual connectors) according to the present disclosure may present one or more advantages relative to conventional tubing connectors. By providing threads on both of the tubing connectors of the tubing connector pair, the tubing connectors according to the present disclosure may be used in those applications requiring or permitting the connectors to be connected or secured together by engaging the threads defined on the separate connectors. By providing a collar that is made of a flexible (e.g., elastic) material and discontinuous threads on at least one of the connectors, it is also possible to connect the connectors without relative rotation of the connectors, such as through the application of a squeezing or expanding force to the collar and sliding the collar over the threaded region of the other connector along a common axis of the tubing connector pair. As a consequence, the tubing connectors according to the present disclosure may be used with those assist devices particular designed for use with connectors lacking a threaded engagement, because the axial motion used in such machines can be applied to the connectors according to the present disclosure without damage to the connectors or the machine. As a further consequence, it would not be necessary for a healthcare provider to carry an inventory of connector assist devices.

It will also be recognized that the structure and operation of the tubing connectors and tubing connector pairs as described herein may applied to the male luer fittings of luer-activated devices (LAD), for example. Other applications for similar connectors incorporating the structure and operation of the connectors described herein will also be recognized.

It should be understood other changes and modifications to the presently preferred embodiments described herein would also be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A medical tubing connector pair comprising:
a female tubing connector; and
a male tubing connector,
the female tubing connector having an external thread and the male tubing connector having an internal thread, the external and internal threads threadingly engaged to secure the female and male tubing connectors together,
the internal thread being made from a flexible material to permit the female and male tubing connectors to be connected to or disconnected from each other without rotation of the tubing connectors relative to each other
at least one of the external and internal threads being discontinuous and threaded regions of the at least one of the external and internal threads being defined on opposing sides of the female tubing connector or the male tubing connector with non-threaded regions disposed between the threaded regions of the at least one of the external and internal threads defined on opposing sides of the female tubing connector or the male tubing connector.

2. The medical tubing connector pair according to claim 1, wherein one of the external and internal threads is discontinuous and the other of the internal and external threads is continuous.

3. The medical tubing connector pair according to claim 1, wherein the male tubing connector comprises a collar, the internal thread defined on an inner surface of the collar.

4. The medical tubing connector pair according to claim 3, wherein the collar is made from a flexible material.

5. The medical tubing connector pair according to claim 1, wherein the flexible material is an elastic material.

6. A medical tubing connector pair comprising:
a female tubing connector; and
a male tubing connector,
the female tubing connector having an external thread and the male tubing connector having an internal thread, the external and internal threads threadingly engaged to secure the female and male tubing connectors together,
the male tubing connector comprises a collar made of a flexible material, the internal thread defined on an inner surface of the collar,
the connector pair has a first mode of engagement wherein the external and internal threads are rotated relative to each other into or out of engagement, and a second mode of engagement wherein the collar is deflected by a squeezing or expanding force to permit the external and internal threads to move axially relative to each other into or out of engagement, and
at least one of the external and internal threads being discontinuous and threaded regions of the at least one of the external and internal threads being defined on opposing sides of the female tubing connector or the male tubing connector with non-threaded regions disposed between the threaded regions of the at least one of the external and internal threads defined on opposing sides of the female tubing connector or the male tubing connector.

7. The medical tubing connector pair according to claim 6, wherein one of the external and internal threads is discontinuous and the other of the internal and external threads is continuous.

* * * * *